United States Patent [19]

Angell et al.

[11] Patent Number: 5,288,367
[45] Date of Patent: Feb. 22, 1994

[54] END-POINT DETECTION

[75] Inventors: David Angell; Carl J. Radens, both of Poughkeepsie, N.Y.

[73] Assignee: International Business Machines Corporation, Armonk, N.Y.

[21] Appl. No.: 11,630

[22] Filed: Feb. 1, 1993

[51] Int. Cl.$^5$ .............................................. G01N 21/00
[52] U.S. Cl. .................................... 156/626; 156/345; 204/192.33; 204/298.32
[58] Field of Search ............... 156/626, 627, 345, 643; 204/298.03, 298.32, 192.13, 192.33; 118/712; 427/10, 8

[56] References Cited

U.S. PATENT DOCUMENTS

| | | | |
|---|---|---|---|
| 4,493,745 | 1/1985 | Chen et al. | 156/626 |
| 4,602,981 | 7/1986 | Chen et al. | 156/627 |
| 4,611,919 | 9/1986 | Brooks | 356/357 |
| 4,846,920 | 7/1989 | Keller | 156/345 |
| 5,014,217 | 5/1991 | Savage | 364/498 |
| 5,097,430 | 3/1992 | Birang | 364/572 |
| 5,160,402 | 11/1992 | Cheng | 156/627 |

FOREIGN PATENT DOCUMENTS

| | | | |
|---|---|---|---|
| 128124 | 6/1987 | Japan | 156/626 |
| 287927 | 11/1989 | Japan | 204/298.32 |
| 296325 | 12/1990 | Japan | 156/626 |

OTHER PUBLICATIONS

Khourky, "Real-Time Etch Plasma Monitor System", IBM Technical Disclosure Bulletin, vol. 25, No. 11A Apr. 1983.
"Partial Least-Squares Regression: A Tutorial" by Paul Geladi and Bruce R. Kowalski, 1986 Elsevier Science Publishers B.V.
Rawlings, John O., "Applied Regression Analysis", Wadsworth & Brooks/Cole 1988.

*Primary Examiner*—Thi Dang
*Attorney, Agent, or Firm*—Richard Lau

[57] ABSTRACT

A wavelength of light is monitored for end-point detection during etching. Spectral data is collected during etching which characterizes variation of light emitted by discharge produced during etching. At least one principal component of the data is calculated. Each principal component has variables, each variable has a weight, and each variable corresponds to a wavelength of the light emitted by the discharge. By examining or analyzing the weights, it is then determined which variable of the principal component varies during etching such that end-point of the etch can be detected by monitoring the wavelength corresponding to the variable.

33 Claims, 5 Drawing Sheets

END-POINT DETECTION

TECHNICAL FIELD

The present invention relates generally to the manufacture of integrated circuit chips and, more particularly, to plasma processing during such manufacture.

BACKGROUND OF THE INVENTION

Typically, during semiconductor processing, a reactive ion etch (RIE) process is employed for etching fine line patterns in a silicon wafer. Reactive ion etching involves positioning a masked wafer in a chamber which contains plasma. The plasma contains etchant gases which are vertically dissociated in an RF field so that reactive ions contained in the etchant gases are accelerated to the wafer surface. The accelerated reactive ions combine chemically with unmasked material on the wafer surface. As a result, volatile etch product is produced. During such etching, a single layer or multiple layers of material or film may be removed. Such material includes, for example, $SiO_2$, poly-silicon, and silicon nitride.

As a film of unmasked material is etched, the volatile etch product is incorporated into the plasma. As the RIE process approaches the interface or end of the film layer being etched, the amount of volatile etch product found in the plasma decreases since the amount of unmasked material being etched is reduced due to the etching. Oftentimes, the amount of volatile etch product in the plasma is tracked in order to determine the end-point of the RIE process, i.e., depletion or decrease in the amount of volatile etch product in the plasma during the RIE process can be used as an indication of depletion of unmasked material being etched for ending the process.

It is also possible to track a reactive species, i.e., one of the etchant or input gasses used to etch the film. As the film is etched, the reactive species will be depleted and relatively low concentrations of the reactive species will be found in the plasma. However, as the film is consumed, the reactive species will be found in the plasma in increasingly higher concentration. A time trace of the optical emission from such a reactive species will show an increase in intensity as the film is etched off.

End-point detection refers to control of an etch step and is therefore an important issue in RIE processes. Tracking the intensity of a wavelength for a particular species using optical emission spectroscopy (OES) is often used for end-point control of a RIE process.

Frequently, OES is used to track the amount of either volatile etch product or reactive species as a function of film thickness. This technique examines emissions from either the volatile etch product or reactive species in the plasma. As the film interface is reached during etching, the emission species related to the etch of the film will either decrease in the case of volatile etch product or increase in the case of reactive species.

More specifically during a RIE process, plasma discharge, i.e., etchant, neutral, and reactive ions in the plasma, is continuously excited by electrons and collisions, thus giving off emissions ranging from ultraviolet to infrared radiation. An optical emission spectrometer diffracts this light into its component wavelengths. Since each species emits light at a wavelength characteristic only of that species, it is possible to associate a certain wavelength with a particular species, and to use this information to detect etch end-point.

As an example, in etching $SiO_2$ with $CHF_3$, carbon combines with oxygen from the wafer to form carbon monoxide as an etch product. It is known that carbon monoxide emits light at a wavelength of 451 nm, and that this wavelength can be monitored for accurately detecting the end-point for such an etch. When the oxide is completely etched there is no longer a source of oxygen and the CO peak at 451 nm decreases, thus signaling end-point.

In the above example, it is known that light emitted from CO at a wavelength of 451 nm should be used for end-point detection. However, such information is generally unavailable, and it has been found to be a formidable task to determine or select the wavelength to use for accurate end-point control. This difficulty exists because of the numerous possibilities for emissions. In other words, any molecule may emit light at a multitude of different wavelengths due to the many transition states available for de-excitation. Therefore, given the process, gases utilized, and the material being etched, it is typically not readily known which wavelength in the spectrum to monitor for end-point control. In this regard, the OES spectrum for a typical RIE etch is composed of hundreds of wavelengths in the visible and ultra-violet bands.

Additionally, there is a present day trend towards using high density plasma sources to replace reactive ion etching. One example is electron cyclotron resonance (ECR), which differs from reactive ion etching in plasma formation. Generally, electron cyclotron resonance operates at a lower pressure than a conventional RIE system, and is therefore able to etch finer-line trenches anisotropically. Comparison studies of the emissions from ECR and RIE plasmas show emphasis on different species and different wavelengths for the same input gas composition. The excitation mechanisms and interactions of the particles at lower pressure account for these differences. The consequence of this for end-point is that the experience and knowledge accumulated from RIE emissions may not carry over to ECR eissions. In other words, it may not be possible to monitor the same species or wavelength for end-point detection in ECR as was monitored for RIE, even if the same material is being etched using the same input gas composition.

Thus, there remains a need in present day and future technology for optimizing selection of a wavelength to monitor for end-point detection during etching.

SUMMARY OF THE INVENTION

Generally, the present invention relates to selecting a wavelength of light to use for end-point detection during etching. Spectral data is collected during etching which characterizes variation of light emitted by discharge produced during etching. At least one principal component of the data is calculated. Each principal component has variables, each variable has a weight, and each variable corresponds to a wavelength of the light emitted by the discharge. By examining or analyzing the weights, it is then determined which variable of the principal component varies during etching such that end-point of the etch can be detected by monitoring the variable, or corresponding wavelength.

DESCRIPTION OF THE DRAWINGS

These and other objects, features, aspects and advantages will be more readily apparent and better understood from the following detailed description of the invention, in which.

DETAILED DESCRIPTION OF THE PREFERRED EMBODIMENT

Figure 1:
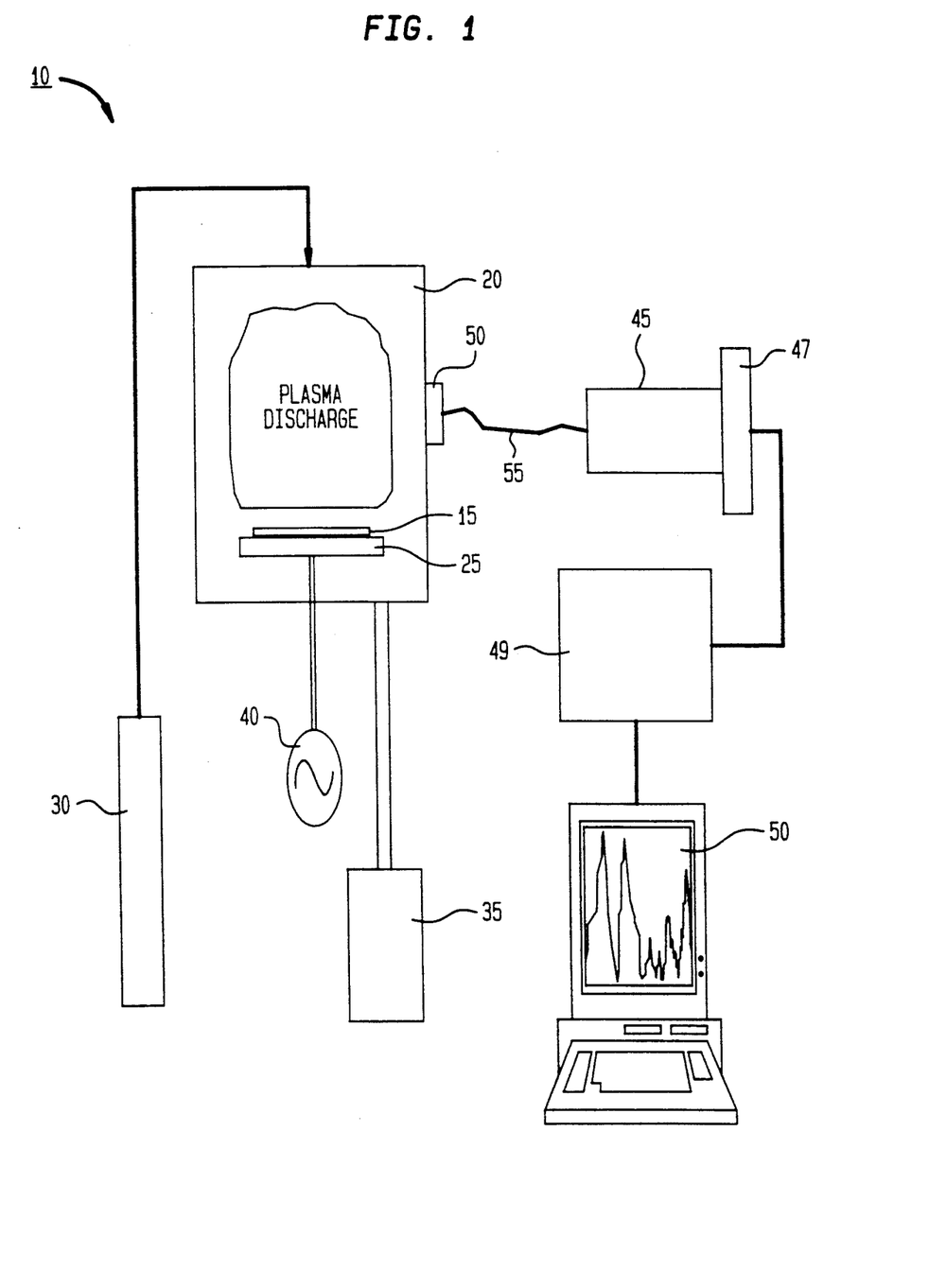
FIG. 1 is a block diagram of major components of the present invention.

Referring initially to FIG. 1, the major components of a typical RIE system 10 are shown. A wafer 15 to be etched, typically a masked wafer, is placed on a cathode 25 inside a plasma chamber 20 filled with plasma. Although the RIE system 10 shown herein is cathode 25 powered, a RIE system in which both the anode and cathode are powered can also be utilized in the practice of the present invention. Further, it should be understood that the present invention is applicable to any plasma etching system, including ECR systems, radio frequency induction systems, etc.

A gas supply 30 provides the necessary etchant gas to the plasma in the plasma chamber 20, and a turbo pump 35 is used for evacuating plasma discharge during etching. An RF generator 40 supplies RF power to the cathode 25 so as to form an RF field in the plasma. The RF field causes reactive ions contained in the etchant gas to accelerate to the surface of the wafer 15. The thus accelerated reactive ions combine chemically with unmasked material on the surface of the wafer 15 so as to form volatile etch product. The volatile etch product is released into the plasma in the plasma chamber 20, and a plasma discharge is formed. Light is emitted from the plasma discharge.

An optical emission spectrometer 45 is attached to the plasma chamber view-port 50 via a fiber optic cable 55. Typically, an optical emission spectrometer is capable of detecting light in a range which encompasses the ultra-violet to the infrared portions of the full electromagnetic spectrum, and thus the term "light" as used herein shall be defined as including all such spectrum possibilities.

Figure 2:
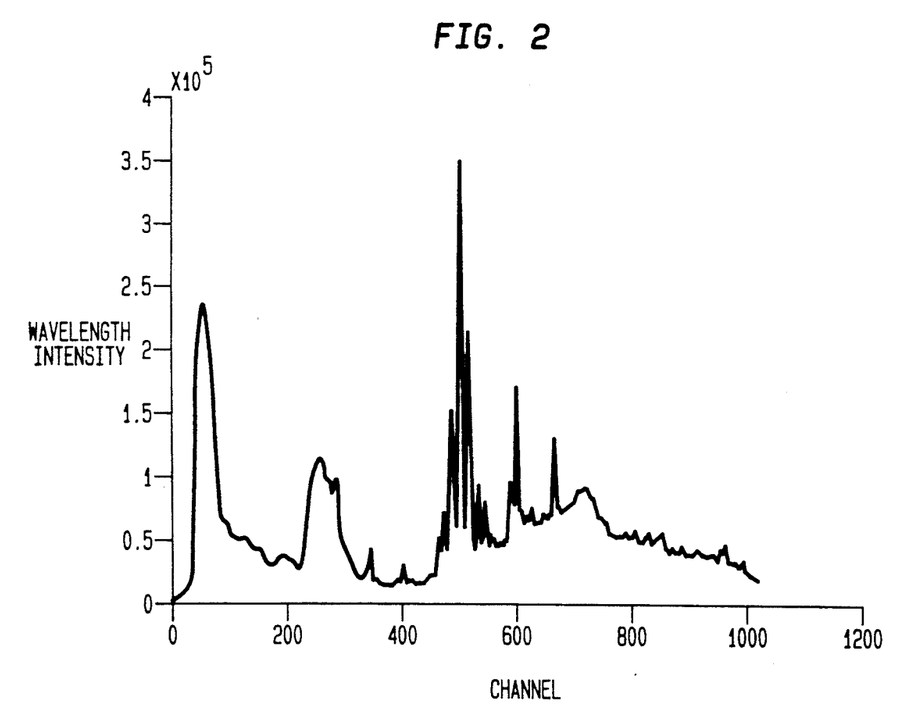
FIG. 2 is a plot of wavelength intensity versus channel of an emission signal at a moment in time during an etch.

The light emitted from the plasma discharge, referred to as an emission signal, is transmitted via the fiber optic cable 55 to a photodiode array detector/DAC (digital-to-analog converter) 47. Each photodiode of the photodiode array detector/DAC 47 can be referred to as a channel, with each channel corresponding to a respective wavelength of light. The photodiode array detector/DAC 47 detects and digitizes the emission signal so that a multi-channel analyzer 49 can track and record the intensity of each wavelength of light at any moment. For example, the spectrum shown in FIG. 2 is a plot of wavelength intensity versus channel at a given moment in time. Digitized spectra can then be sent to a computer 50 for further processing in accordance with the present invention.

In order to obtain representative spectra for use in accordance with the present invention, wavelength intensity for each channel is continually tracked and recorded from the beginning of the RIE process being analyzed to a point in time beyond the ending point of the required etch. For such purpose, an initial experimental etch may be required to be conducted. As an example, wavelength intensity for each channel can be tracked and recorded for each second of etching, thus creating a spectrum for each second. Completion of the required etching can be confirmed by slicing the wafer 15 apart and examining the wafer 15 using, for example, a scanning electron microscope.

Using the information thus tracked and recorded, a concatenated file can be created by successively appending the most recent spectrum to the preceding spectrum, thus creating a file which represents the temporal behavior of each channel or photodiode. In this regard, each photodiode or channel can be translated to a corresponding wavelength by correlation of channel to wavelength for a known reference spectra.

Figure 3:
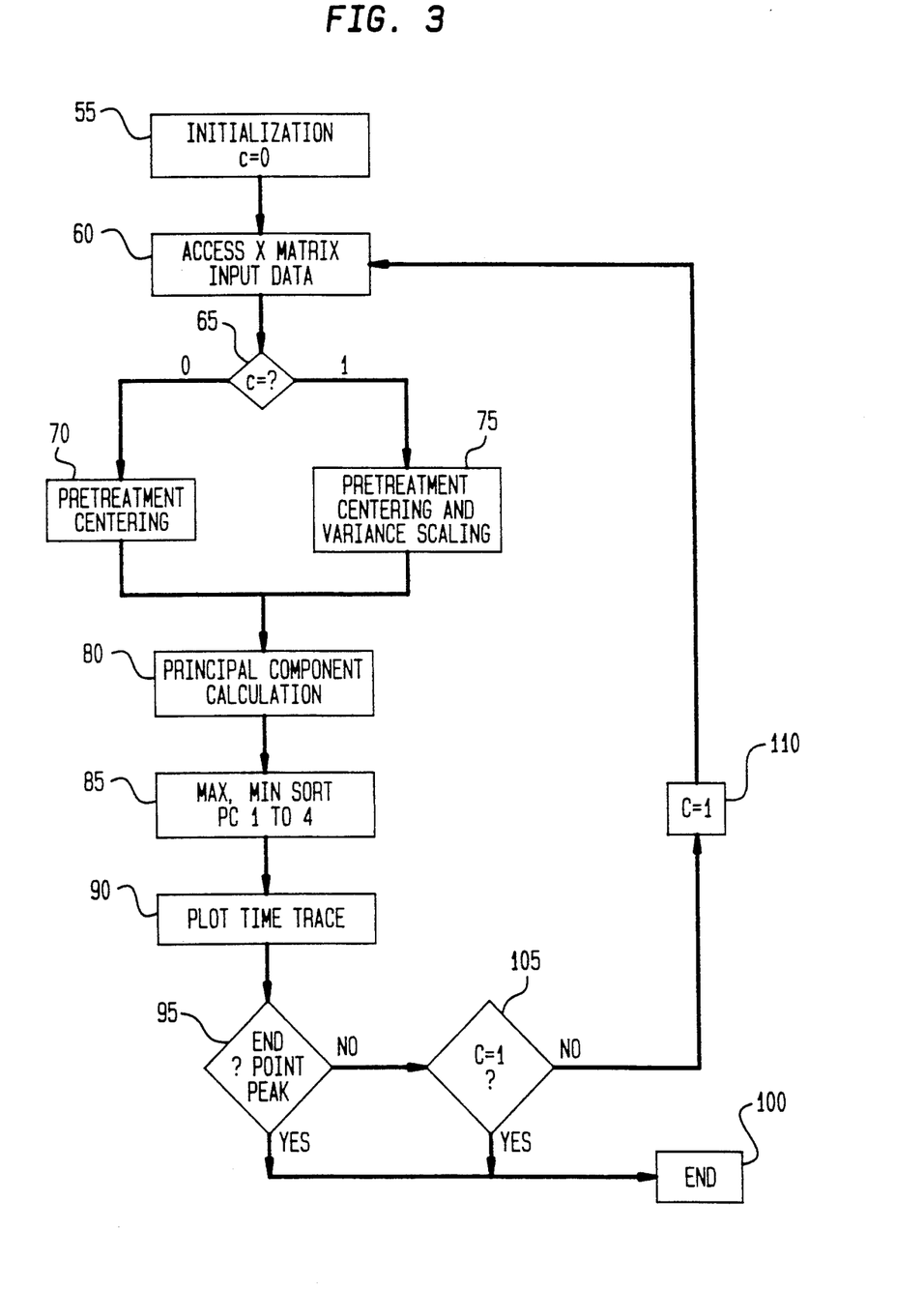
FIG. 3 is a flow diagram of the present invention.

After the data is collected, the input data is stored in the computer 50 as a matrix, hereinafter referred to as the X matrix, and the X matrix is then processed in accordance with the steps outlined in the flowchart shown in FIG. 3, and explained in greater detail hereinbelow.

At initialization block 55, the value 0 is assigned to a variable C. The input data or X matrix is then accessed at block 60, and depending upon the value of variable C at block 65, the input data will either be pretreated at block 70 or at block 75. In this regard, in the initial pass, the input data will be pretreated at block 70 and processed therefrom and, as explained hereinbelow, if a satisfactory peak cannot be determined for end-point detection by pretreatment at block 70, then the value 1 is assigned to the variable C, and the input data is re-accessed, pretreated at block 75 and processed therefrom.

Pretreatment at block 70 involves centering, and pretreatment at block 75 involves centering and variance scaling. Centering of the input data at either pretreatment block 70 or 75 allows for more convenient or simplified analysis of the plot of principal component variable weights versus channel by characterizing the weights relative to zero, rather than another reference point. However, such a plot is not required to be generated for the present invention to be operational (explained hereinafter), and analysis of such a plot can still be performed without centering the input data. Therefore, it should be understood that centering at either pretreatment block 70 or 75 is not a necessary requirement for the present invention. Accordingly, pretreatment block 70 should be considered an optional step in the practice of the invention.

Centering is accomplished by determining the mean of each column of the X matrix, and subtracting each mean from each element of its corresponding respective column.

In the next step, at block 80, principal component analysis is performed on the input data. Principal component analysis allows for determination of which channel varies during etching in such a manner that end-point of the etch can be detected by monitoring such channel. Although other methods may exist, three methods for computing principal components are as follows:
1. eigenanalysis (EIG);
2. singular value decomposition (SVD); and
3. nonlinear partial least squares (NIPALS).

Each of the first two methods, EIG and SVD, simultaneously calculate all possible principal components, whereas the NIPALS method allows for calculation of one principal component at a time. There are as many principal components as there are channels. It has been observed that if determination of which channel can be used for end-point detection cannot be made after analysis of approximately the first four principal components, then there is reasonable likelihood that the input data presented has no useful information for end-point detection. Thus, since the number of principal components to be calculated can typically be limited to approximately the first four principal components, the NIPALS method is preferable from the standpoint of efficient usage of computing time. However, it should be fully understood that this invention does not require NIPALS to be used for principal component analysis and it may be preferable to use one of the first two methods, EIG or SVD, if a significant number of principal components needs to be calculated, and thus NIPALS is shown herein for exemplary purposes only. See *Applied Regression Analysis*, by John O. Rawlings, "Introduction to Matrices", pp. 50–60, published by Wadsworth & Brooks/Cole, 1988 for discussion on the EIG and SVD methods, and see "Partial Least-Squares Regression: A Tutorial", by P. Geladi and B.R. Kowalski, *Analytica Chimica Acta*, Vol. 185, pages 1–17, published by Elsevier Science Publishers B.V., Amsterdam, 1986, for discussion on the NIPALS method.

In more detail, principal component analysis is a method of writing a matrix, such as matrix X, wherein matrix X is comprised of 1 to n columns and 1 to l rows, of rank r, where r is the number of variables in matrix X, as a sum of r rank 1 matrices, as follows:

$$X = m_1 + m_2 + m_3 + m_4 + \ldots + m_r$$

These rank 1 matrices, $m_k$, where k is any integer 1 through r, can be written as the product of two vectors, a score vector, $t_k$, and a principal component vector (commonly referred to merely as "principal component"), $p'_k$, where the prime notation designates transposition of the vector for preparation for the vector multiplication operation, as follows:

$$X = t_1 p'_1 + t_2 p'_2 + \ldots + t_k p'_k$$

As stated hereinabove, the NIPALS method allows for calculation of one principal component at a time. More specifically, once the first principal component, $p'_1$, is calculated as explained hereinbelow, then the outer product, $t_1 p'_1$, is subtracted from X and the residual, $E_1$, is calculated in order to calculate the next or second principal component, $p'_2$, and as before the new outer product $t_2 p'_2$ is substracted from $E_1$, thus yielding $E_2$. This is an iterative procedure in that each subsequent principal components can be calculated using the previous principal component, as follows:

$$E_1 = X - t_1 p'_1$$

$$E_2 = E - t_2 p'_2$$

$$E_k = E_{k-1} - t_k p'_k$$

The NIPALS algorithm proceeds as follows:
1. Take any vector $x_j$ from X, wherein j is any one of the column vectors 1 to n of matrix X, and call it $t_h$, wherein h represents the number of the principal component being calculated, wherein $t_h = x_j$
2. calculate $p'_h$:

$$p'_h = t_h X / t_h' t_h$$

3. normalize $p'_h$ to unit length:

$$p_{hnew} = p'_h / ||p'_h||$$

4. Calculate $t_h$:

$$t_h = X p_{hnew} / p'_{hnew} p_{hnew}$$

5. Compare the $t_h$ used in step 2 with that obtained in step 4. If the $t_h$ used in step 2 with that obtained in step 4 are the same, or within a preset allowable error, then the current principal component has been satisfactorily calculated, and the procedure is concluded. If the $t_h$ used in step 2 with that obtained in step 4 are different, or are not within the preset allowable limit, then the current principal component has not been satisfactorily determined and the procedure is continuously repeated beginning from step 2, until a satisfactory principal component is determined.

Subsequent to calculating the principal components $p'_k$ at block 80, the next step at block 85 is to rank or sort the weights of the variables of each principal component from maximum to minimum values. Such ranking provides information as to which variables, if any, of each principal component have opposing behavioral patterns. Generally, the variables that are of greatest value will behave in opposite manner from the variables that are of lowest value. As will be explained in greater detail hereinafter, this analysis allows for determination of which variable, or channel or wavelength corresponding to such variable, has a behavioral pattern during etching that can be used for end-point detection.

If desired, a plot of the weights of the principal component variables versus channel can be created which will show which variables have opposing behavioral patterns. The variable(s) that behaves in opposite manner from the majority of the variables will show up in the plot as a peak(s). Analysis of the pattern of the variables can be interpreted as being similar to formation of a correlation matrix using all variables of the X matrix. For example, in the case of nearly equal matrix variables, with only slight differences in any element, the above analysis would produce a plot that is nearly a horizontal line, and it would be known that all variables behave in substantially the same manner, with no variable having an opposing behavioral pattern from the other variables. On the other hand, in the situation where an array of samples has only one variable which is "different" from the others, the plot will be a horizontal line with a single spike or peak at the variable that differs in behavior.

Figure 4:
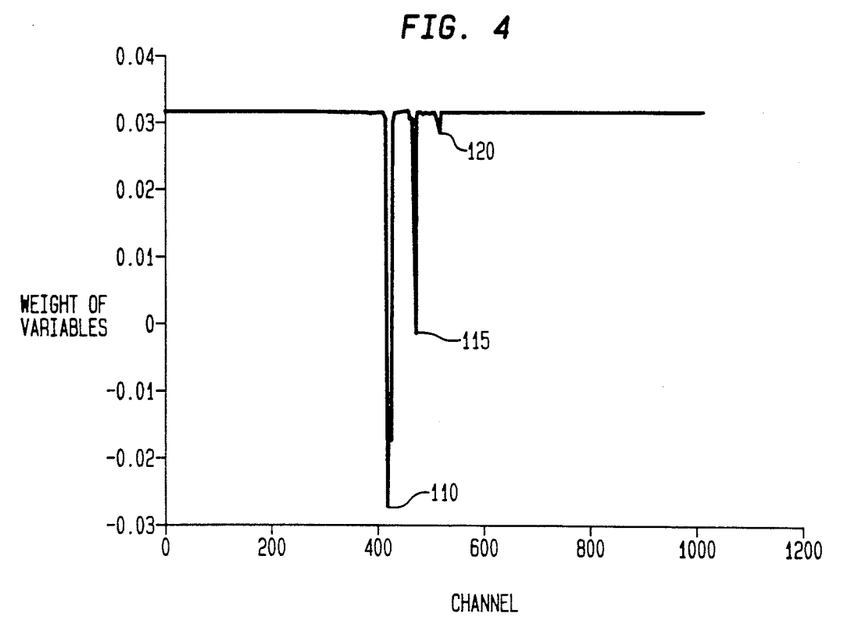
FIG. 4 is a plot of weights of variables of a principal component versus channel generated from data collected during an etch.

By way of illustration, FIG. 4 shows a plot of the weights of the variables of a first principal component versus channel for OES data collected from a polysilicon etch. Of course, each principal component calculated at block 80 will have its own plot. It can be observed in FIG. 4 that there are two peaks 110,115, and that the variables corresponding to these peaks 110,115 have the lowest value relative to the other variables. Since peak 120 is minor or insignificant relative to peaks 110 and 115, this peak 120 can be disregarded for end-point purposes. The remainder of the plot is relatively flat. From this plot, it is known that the behavioral patterns of the channels or variables corresponding to peaks 110 and 115 do no correlate with behavioral patterns of the other channels. In this regard, the channels corresponding to peaks 110 and 115 will each have a time trace (which tracks channel or wavelength behavior) which differs from the time traces of the channels corresponding to the substantially level portions of the plot. In other words, the time trace of each channel that corresponds to the substantially level portions of the plot will each behave in a substantially consistent manner, although such consistent manner is not determinable by the plot, and the time trace of the channels that correspond to the peaks 110,115 will behave in an opposite manner. Advantageously, the information for end-point from the entire X matrix is compressed into the single 2-dimensional plot shown in FIG. 4, and allows for peak information to be readily extracted therefrom.

As indicated at block 90, a time trace or plot of intensity versus time for the variable(s) having weight of maximum value and the variable(s) having weight of minimum value as found in the sorting step can then be created. The exact number of time traces that need to be created and examined is a matter of results, i.e., depends on the number of peaks that are in the plot of FIG. 4. As a general rule, the best peaks or channels for end-point detection are those that exhibit clearly and distinctly different behavior from the rest of the channels. As mentioned hereinabove, in practice, it has been found that if such a peak is not found after analysis of approximately the first four principal components, then there is little probability that the input data being utilized will yield any peaks that will be satisfactory for end-point control purposes.

Figure 5:
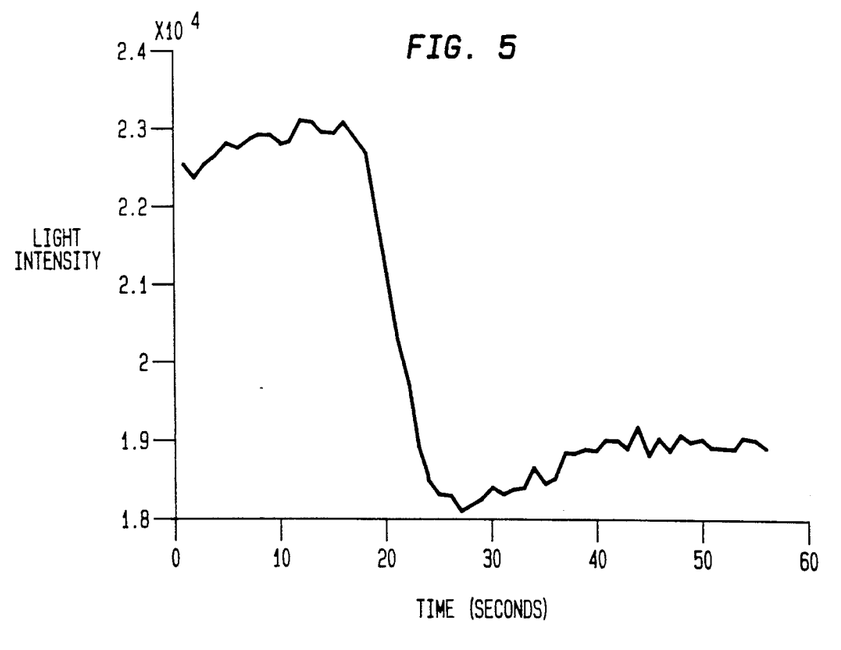
FIG. 5 is a time trace of a channel corresponding to a peak of the plot shown in FIG. 4.

FIG. 5 shows a time trace, light intensity versus wavelength, of the variable corresponding to peak 110, which is the variable of minimum value. Specifically, peak 110 corresponds to variable or channel 417. Note the drop-off in intensity of the time trace over the relatively short period of time, approximately 10 seconds. In this regard, the intensity must drop off within a certain period of time in order to qualify as being an acceptable end-point peak. The specific acceptable range of intensity drop-off and time period is chosen by the process engineer. Generally, the time trace shown in FIG. 5 is considered acceptable for end-point detection purposes and, thus, peak 110 is satisfactory.

Figure 6:
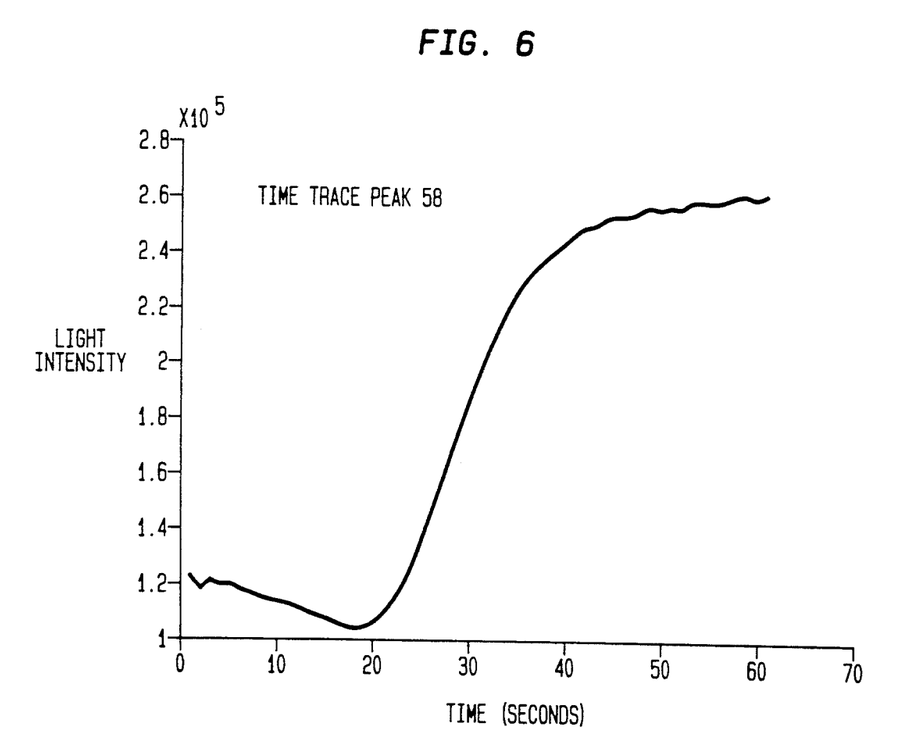
FIG. 6 is a time trace of a channel corresponding to a substantially level portion of the plot shown in FIG. 4.

Compare the time trace of FIG. 5, i.e., the peak 110, with the time trace of any of the channels corresponding to the level portions of the plot of FIG. 4. Any of the channels corresponding to the level portions can be considered maximum values and will have a rising time trace, such behavior being opposite in manner relative to the channel 417 corresponding to the peak 110. For example, FIG. 6 shows a time trace of one of these channels, such as channel 58. Note that the time trace of any of the channels corresponding to the level portions of the plot will rise in substantially similar manner to the time trace shown in FIG. 6. Those skilled in the art will recognize that this time trace cannot be used for accurate end-point detection. Specifically, the relatively lengthy time period, approximately 20–30 seconds, for completion of the rise or transition is considerably greater than the time typically required for complete etching of a film. Note the relatively shorter time period for intensity drop-off of channel 110, approximately 10 seconds, which is more representative of the time required for completion of an etch. Since all channels corresponding to the level portions of the plot behave similarly to the time trace of channel 58, none of these channels can be used for end-point detection purposes.

As indicated at block 95, if a satisfactory peak is found, then the procedure is terminated at block 100. However, if a satisfactory peak is not found, then it is determined at block 105 what value has been assigned to the variable C. If the variable C has a value of 1, then it is known that the input data has already been through two passes, with pretreatment at block 70 in the first pass and pretreatment at block 75 in the second pass, and the procedure is terminated at block 100. Note that if there is no information relevant to end-point in the original input data, then there will not be any "good" candidates for end-point peaks, and the procedure would terminate after two passes. However, if the variable C has a value of 0, then the input data has only been through one pass. In this situation, the variable C is re-assigned the value 1 at block 110, and the input data is re-accessed at block 60. Since the variable C now has a value of 1, the input data is pretreated at block 75, and the procedure continues in the manner as described above.

At block 75, pretreatment of the input data involves centering and variance scaling. Similar to pretreatment at block 70, centering is optional for pretreatment at block 75. As explained hereinabove, centering is accomplished by determining the mean of each column of the X matrix, and then subtracting the mean from each element of its corresponding respective column. Variance scaling involves calculating the standard deviation of each column, and dividing each column standard deviation into each element of its respective column. This allows variance of the input data to be analyzed and compared relative to each other, rather than analysis and comparison of the absolute variance of the input data. Since variance scaling is not always necessary for analysis, for efficiency purposes, variance scaling is conducted only after an attempt has been made to analyze and compare the data without variance scaling.

While the invention has been described in terms of specific embodiments, it is evident in view of the foregoing description that numerous alternatives, modifications and variations will be apparent to those skilled in the art. Thus, the invention is intended to encompass all such alternatives, modifications and variations which fall within the scope and spirit of the invention and the appended claims.

What is claimed is:

1. A method of selecting a wavelength of light to monitor for end-point detection during etching, wherein the etching produces discharge which emits light, said method comprising the steps of:
   collecting data during etching, said data characterizing variation of light emitted by discharge produced during the etching;
   calculating a principal component of the data, said principal component having variables, each variable having a weight, and each variable corresponding to a wavelength of the light emitted by the discharge; and
   determining which variable of the principal component varies during the etching such that end-point of the etch can be detected by monitoring the wavelength corresponding to the variable.

2. A method according to claim 1, further comprising the step of centering the data prior to the step of calculating a principal component of the data.

3. A method according to claim 2, further comprising variance scaling the data subsequent to centering the data.

4. A method according to claim 1, wherein said step of calculating a principal component of the data comprises calculating no more than the first four principal components of the data.

5. A method according to claim 1, wherein said step of calculating a principal component of the data comprises using the eigenanalysis method.

6. A method according to claim 1, wherein said step of calculating a principal component of the data comprises using the singular value decomposition method.

7. A method according to claim 1, wherein said step of calculating a principal component of the data comprises using the nonlinear partial least squares method.

8. A method according to claim 1, wherein said step of determining comprises ranking the variables according to weight from maximum value to minimum value, and analyzing the behavioral pattern of the variable having weight of maximum value and the variable having weight of minimum value.

9. A method according to claim 8, wherein the ranking of the variables includes plotting the weights of the principal component variables versus variable.

10. A method according to claim 8, wherein the analyzing of behavioral pattern includes plotting the time trace of the variable having weight of maximum value and the time trace of the variable having weight of minimum value.

11. A method according to claim 1, wherein said step of collecting data during etching includes use of an optical emission spectrometer.

12. A method of etching a wafer, comprising the steps of:
    etching a wafer such that discharge is produced which emits light; and
    terminating etching of the wafer when light of a predetermined wavelength emitted by the discharge varies so as to signal end-point of the etch, wherein determining of the predetermined wavelength comprises the steps of:
    performing an experimental etch;
    collecting data during the experimental etch, said data characterizing variation of light emitted by the discharge produced during the experimental etch;
    calculating a principal component of the data, said principal component having variables, each variable having a weight, and each variable corresponding to a wavelength of the light emitted by the discharge; and
    determining which variable of the principal component varies during the experimental etch such that end-point can be detected by monitoring the wavelength corresponding to the variable, said wavelength being the predetermined wavelength.

13. A method according to claim 12, further comprising the step of centering the data prior to the step of calculating a principal component of the data.

14. A method according to claim 13, further comprising variance scaling the data subsequent to centering the data.

15. A method according to claim 12, wherein said step of calculating a principal component of the data comprises calculating no more than the first four principal components of the data.

16. A method according to claim 12, wherein said step of calculating a principal component of the data comprises using the eigenanalysis method.

17. A method according to claim 12, wherein said step of calculating a principal component of the data comprises using the singular value decomposition method.

18. A method according to claim 12, wherein said step of calculating a principal component of the data comprises using the nonlinear partial least squares method.

19. A method according to claim 12, wherein said step of determining comprises ranking the variables according to weight from maximum value to minimum value, and analyzing the behavioral pattern of the variable having weight of maximum value and the variable having weight of minimum value.

20. A method according to claim 19, wherein the ranking of the variables includes plotting the weights of the principal component variables versus variable.

21. A method according to claim 19, wherein the analyzing of behavioral pattern includes plotting the time trace of the variable having weight of maximum value and the time trace of the variable having weight of minimum value.

22. A method according to claim 12, wherein said step of collecting data during etching includes use of an optical emission spectrometer.

23. An apparatus for selecting a wavelength of light to monitor for end-point detection during etching, wherein the etching produces discharge which emits light, said apparatus comprising:
    means for collecting data characterizing variation of light emitted by discharge produced during etching;
    means for calculating a principal component of the data, said principal component having variables, each variable having a weight, and each variable corresponding to a wavelength of the light emitted by the discharge; and
    means for determining which variable of the principal component varies during etching such that end-point of the etch can be detected by monitoring the wavelength corresponding to the variable.

24. An apparatus according to claim 23, further comprising means for centering the data.

25. An apparatus according to claim 24, further comprising means for variance scaling the data.

26. An apparatus according to claim 23, wherein said means for calculating a principal component of the data calculates no more than the first four principal components of the data.

27. An apparatus according to claim 23, wherein said means for calculating a principal component of the data uses the eigenanalysis method.

28. An apparatus according to claim 23, wherein said means for calculating a principal component of the data uses the singular value decomposition method.

29. An apparatus according to claim 23, wherein said means for calculating a principal component of the data uses the nonlinear partial least squares method.

30. An apparatus according to claim 23, wherein said means for determining comprises means for ranking the variables according to weight from maximum value to minimum value, and means for analyzing the behavioral pattern of the variable having weight of maximum value and the variable having weight of minimum value.

31. An apparatus according to claim 30, wherein said means for ranking the variables includes means for plotting the weights of the principal component variables versus variable.

32. An apparatus according to claim 30, wherein said means for analyzing the behavioral pattern includes means for plotting the time trace of the variable having weight of maximum value and the time trace of the variable having weight of minimum value.

33. An apparatus according to claim 23, wherein said means for collecting data during etching comprises an optical emission spectrometer.

* * * * *